United States Patent
Tashiro et al.

(10) Patent No.: US 7,531,796 B2
(45) Date of Patent: May 12, 2009

(54) FOCUSED ION BEAM APPARATUS AND SAMPLE SECTION FORMING AND THIN-PIECE SAMPLE PREPARING METHODS

(75) Inventors: Junichi Tashiro, Chiba (JP); Yutaka Ikku, Chiba (JP); Toshiaki Fujii, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 123 days.

(21) Appl. No.: 11/840,575

(22) Filed: Aug. 17, 2007

(65) Prior Publication Data

US 2008/0042059 A1   Feb. 21, 2008

(30) Foreign Application Priority Data

Aug. 21, 2006   (JP) ............................. 2006-224191

(51) Int. Cl.
*H01J 37/305* (2006.01)
*H01J 37/30* (2006.01)
*G01N 23/22* (2006.01)

(52) U.S. Cl. ....................... 250/306; 250/307; 250/310; 250/396 R; 250/397; 250/423 R; 250/492.2; 250/492.3

(58) Field of Classification Search ................. 250/306, 250/307, 310, 396 R, 397, 423 R, 492.2
See application file for complete search history.

(56) References Cited

U.S. PATENT DOCUMENTS 5,055,696 A  * 10/1991  Haraichi et al. .......... 250/492.2
6,146,797 A  * 11/2000  Fujii ........................... 430/30
7,423,266 B2 * 9/2008  Tashiro et al. ............... 250/310

FOREIGN PATENT DOCUMENTS

JP   11-273613   10/1999

* cited by examiner

*Primary Examiner*—Nikita Wells
(74) *Attorney, Agent, or Firm*—Brinks Hofer Gilson & Lione

(57) ABSTRACT

Detected is a secondary electron generated by irradiating a focused ion beam while performing etching a sample section and the around through scan-irradiating the focused ion beam. From a changing amount of the detected secondary electron signal an end-point detecting mechanism detects an end point to thereby terminate the etching, so that a center position of a defect or a contact hole is effectively detected even with an FIB apparatus not having a SEM observation function.

6 Claims, 9 Drawing Sheets

FOCUSED ION BEAM APPARATUS AND SAMPLE SECTION FORMING AND THIN-PIECE SAMPLE PREPARING METHODS

This application claims priority under 35 U.S.C. §119 to Japanese Patent Application No. JP2006-224191 filed Aug. 21, 2006, the entire content of which is hereby incorporated by reference.

BACKGROUND OF THE INVENTION

The present invention relates to forming a sample section and working a TEM sample by use of a focused ion beam apparatus.

Using FIG. 9, explanation is made on an observation method of working a defect region with use of a conventional FIB-SEM apparatus. At first, a sample 22 is worked by irradiating an ion beam IB, to form a rectangular opening 21. After forming the opening, an electron beam EB is scan-irradiated to a section D. By detecting a secondary electrons generated at that time, a secondary electron image is observed as to the section D. In order to acquire a section through a defect center in defect analysis, two points are specified in an end of a particular structure within an acquired secondary electron image. Then, the particular structure is gradually milled by an ion beam IB, to measure the end-to-end distance of the specific structure in the milling. By terminating the milling with the ion beam IB at a time the change of distance becomes nearly zero, a section can be acquired in the center region of the defect.

[Patent Document 1] JP-A-H11-273613

In the foregoing defect observation-by-working method using the conventional FIB-SEM apparatus, there is a need to irradiate an electron beam to a sample section in order to detect a center position of a defect or a contact hole. This requires an FIB-SEM apparatus having a SEM column. Meanwhile, because of working with an FIB and confirming an end point by switching the irradiation beam to SEM, it takes time in switchover. The present invention is to provide a sample section forming method for effectively detecting a center position of a defect or a contact hole even with an FIB apparatus not having a SEM observation function. Meanwhile, it is an object to provide a method to efficiently prepare a thin-piece sample such that the center of a defect or a contact hole comes to a center of an observing thin-piece sample for a TEM or the like.

SUMMARY OF THE INVENTION

In order achieve the foregoing object, used is a method of forming a sample section containing at least two different materials with respect to a direction parallel with a sample surface by use of a focused ion beam apparatus, the sample section forming method using a focused ion beam apparatus comprising: a step of detecting a secondary charged particle generated by irradiating the focused ion beam while performing etching on a desired region of a sample by scan-irradiating a focused ion beam while forming a section vertically to the sample surface; and a step of detecting a change of signal amount by means of a signal of the detected secondary charged particle and terminating the etching depending upon the change amount. In other words, using s focused ion beam apparatus, a focused ion beam is scan-irradiated to a desired region of the sample surface in a direction parallel with the axis of the lens barrel of the focused ion beam apparatus, thereby forming a sample section. When a sample surface containing a different material appears upon forming a section while forming the sample section, there are included a step of detecting a secondary charged particle generated by irradiating the focused ion beam while performing etching on the sample desired region through scan-irradiating the focused ion beam when a sample section containing a different material appears during forming a section while forming the sample section, and a step of detecting a signal amount change according to a signal of the detected secondary charged particle and terminating the etching depending upon the change amount thereof. Otherwise, it can be a method of forming a section in a sample surface by san-irradiating a focused ion beam in a direction parallel with an axis of a lens barrel of a focused ion beam apparatus and forming a sample section in a desired region of a sample while etching the section, the sample section forming method using a focused ion beam apparatus characterized by including: a step of detecting a secondary charged particle generated by irradiating the focused ion beam; and a step of detecting a signal amount change of a detected signal of the secondary charged particle and terminating the etching depending upon the change amount when there is a change of signal amount.

The second problem-solving means uses a sample section forming method using a focused ion beam apparatus according to claim 1, wherein the desired region is established to have one side nearly parallel with one side of the desired section in the sample surface, to perform etching in a manner forming a section including the parallel one side, followed by performing etching on the working region with scan-irradiating the focused ion beam while forming a section of the working region toward the desired section and in a direction broadening, so that a signal amount change at each sectional position is detected based on a signal of secondary charge particles generated at this time, depending upon a change amount of which the etching is terminated.

The third problem-solving means uses a sample section forming method using a focused ion beam apparatus according to claim 1 or 2, wherein the step of terminating the etching by detecting a signal amount change with the detected secondary charged particle signal includes cumulating with respect to the sub-scanning direction a secondary charged particle signal detected in the etching in a main scanning direction at each sub-scanning position provided that a direction nearly parallel with one side of the desired section is taken as the main scanning direction and a direction vertical to the main direction as the sub-scanning direction, detecting a change of the cumulated signal amount, and terminating the etching depending upon a change amount thereof.

The fourth problem-solving means a thin-piece sample preparing method using a focused ion beam apparatus characterized by: a step of forming a sample section by using a sample section forming method using a focused ion beam apparatus according to any one of the first to third problem-solving means; and forming similarly a section oppositely to the formed sample section with respect to a desired thin-piece sample region, to form a thin-piece sample region.

The fifth problem-solving means uses a focused ion beam apparatus comprising: an ion generation source for generating ions; an ion optical system that restricts the ions into a focused ion beam and irradiating, while scanning, the focused ion beam to the sample surface; a sample table for supporting a sample; a sample-table control mechanism for moving the sample table; a secondary charged particle detector that detects a secondary charged particle generated by irradiating the focused ion beam; and an end-point detecting mechanism that detects an end point from the change amount of a secondary charged particle signal amount detected at the secondary charged particle detector when proceeding an etching on a section formed vertically to the sample flat surface by scan-irradiating the focused ion beam.

The operation based on the first problem-solving means is as follows. By terminating the etching through detecting a change of a detected secondary charged particle signal amount, working can be ended in a state exposing a desired section containing different materials.

The operation based on the second problem-solving means is as follows. By establishing and etching a working region through taking, as one side, a plane nearly parallel with a desired sample section and broadening the working region toward the desired sample section until detecting a etch termination signal, a desired section can be formed without encountering a deficiency or an excess of working.

The operation based on the third problem-solving means is as follows. Even where secondary charged particle signal is small in amount or signal amount change is not easily to detect, working can be terminated in a state exposing a desired section by cumulating secondary charged particles signals and detecting a change in the cumulated signal amount.

The operation based on the fourth problem-solving means is as follows. By similarly forming a section oppositely to the formed sample section with respect to a desired thin-piece sample region, a thin-piece sample can be prepared in the desired thin-piece sample region.

The operation based on the fifth problem-solving means is as follows. By using a focused ion beam apparatus having an end-point detecting mechanism that detects an end point from the detected secondary charged particle signal, working can be terminated in a state exposing the desired section containing different materials.

As described above, according to a focused ion beam apparatus of the invention and sample section forming method using the focused ion beam apparatus, by terminating etching through detecting a signal amount change of a generated secondary charged particle while performing etching, a defect or a contact-hole center position seen from above can be detected even with an FIB apparatus not having a SEM observation function, thus forming a sample section with efficiency. Meanwhile, according to the focused ion beam apparatus of the invention and thin-piece sample preparing method using the focused ion beam apparatus, a thin-piece sample for TEM-observation can be efficiently prepared in the center of which a defect or the center axis of a contact-hole lies, even in an FIB apparatus not having a SEM observation function.

DETAILED DESCRIPTION OF THE PREFERRED EMBODIMENTS

Based on FIGS. 1 to 7, explanation will be now made on an embodiment of the present invention.

Figure 1:
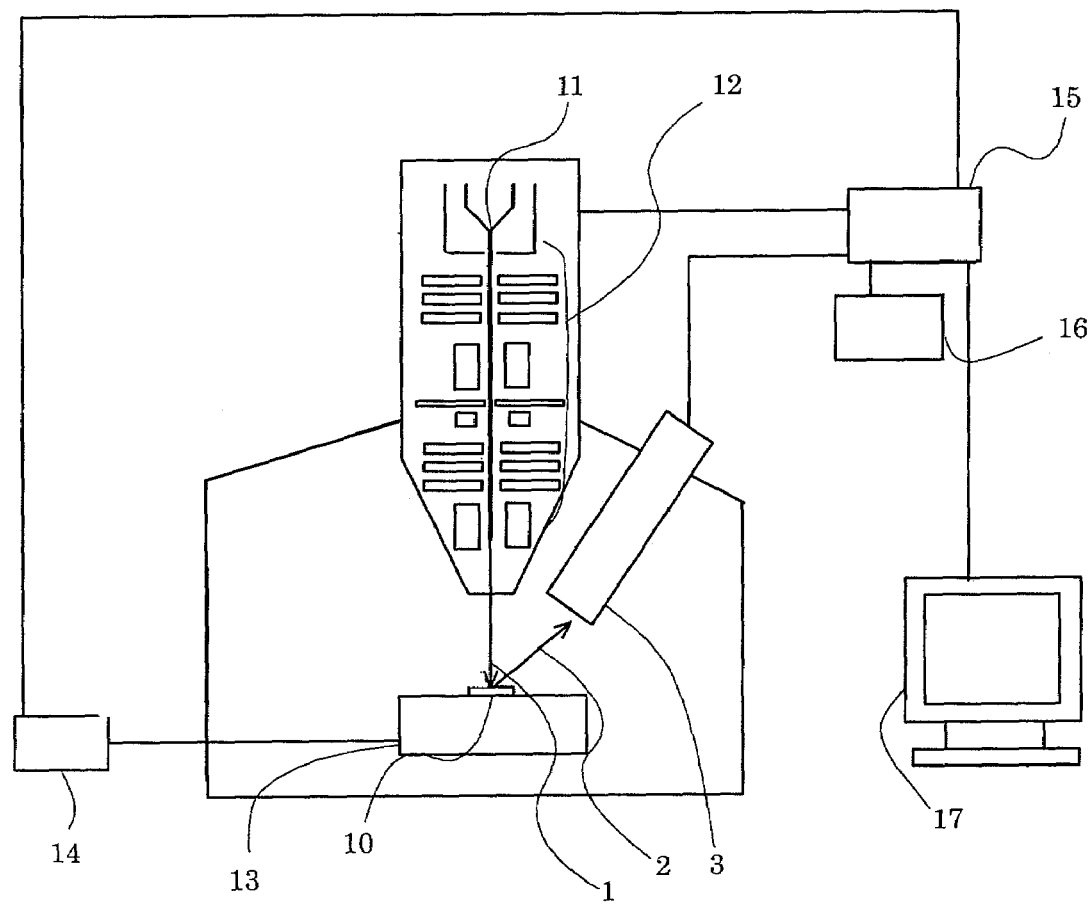
FIG. 1 is a schematic diagram of an FIB apparatus showing an embodiment of the present invention.

FIG. 1 is a schematic diagram of an FIB apparatus showing an embodiment of the invention. The ions, generated by the ion source 11, are collected by an ion optical system 12 into a focused ion beam 1 and scan-irradiated to a sample 10 like a semiconductor device. The sample 10, rested on a sample stage 13, can be moved by a stage drive mechanism 14. The secondary electron 2, that is a secondary charged particle generated by irradiating a focused ion beam 1 to the sample 10, is to be detected by a secondary electron detector 3 serving as a secondary charge detector. From the signal of a secondary electron detected, a secondary electron image of the sample 10 is to be displayed on a display 17. Meanwhile, an end-point detecting mechanism 16 can detect an end point depending upon a change amount from the detected signal amount of secondary electrons during working.

Using FIGS. 2A-2D, 3A-3D and 6, explanation is made on a case to observe the section including the axis of a contact hole.

FIGS. 2A-2D are sample surface views showing an embodiment of the invention. In a sample 10 covered with a surface protection film 4, there are included an interlayer film 6 formed of insulator and a metal contact hole 7 provided vertical to the sample surface. The contact hole 7 cannot be observed from the sample surface. The contact hole 7, if it is cut along a plane parallel with the sample surface, there exists different regions of materials like insulator and metal, in a direction of the cut surface.

FIGS. 3A-3D show a relationship between a position and a cumulative secondary-electron signal amount wherein the axis of abscissa represents a position in a main scanning direction provided that the direction nearly parallel with one side of a section is taken as a main scanning direction and the direction nearly vertical to the main scanning direction as a sub-scanning direction while the axis of ordinate indicates a secondary-electron signal amount cumulated in the sub-scanning direction. Here, secondary-electron signal amount cumulation refers to summing up, in amount, the secondary-electron signals detected at respective sub-scanning directional positions relative to the main scanning direction. Despite there is a difficulty in detecting a secondary electron amount change under a certain condition of sample material and focused ion beam irradiation, a change can be confirmed clearly by summing up the secondary-electron signal amounts.

Figure 6:
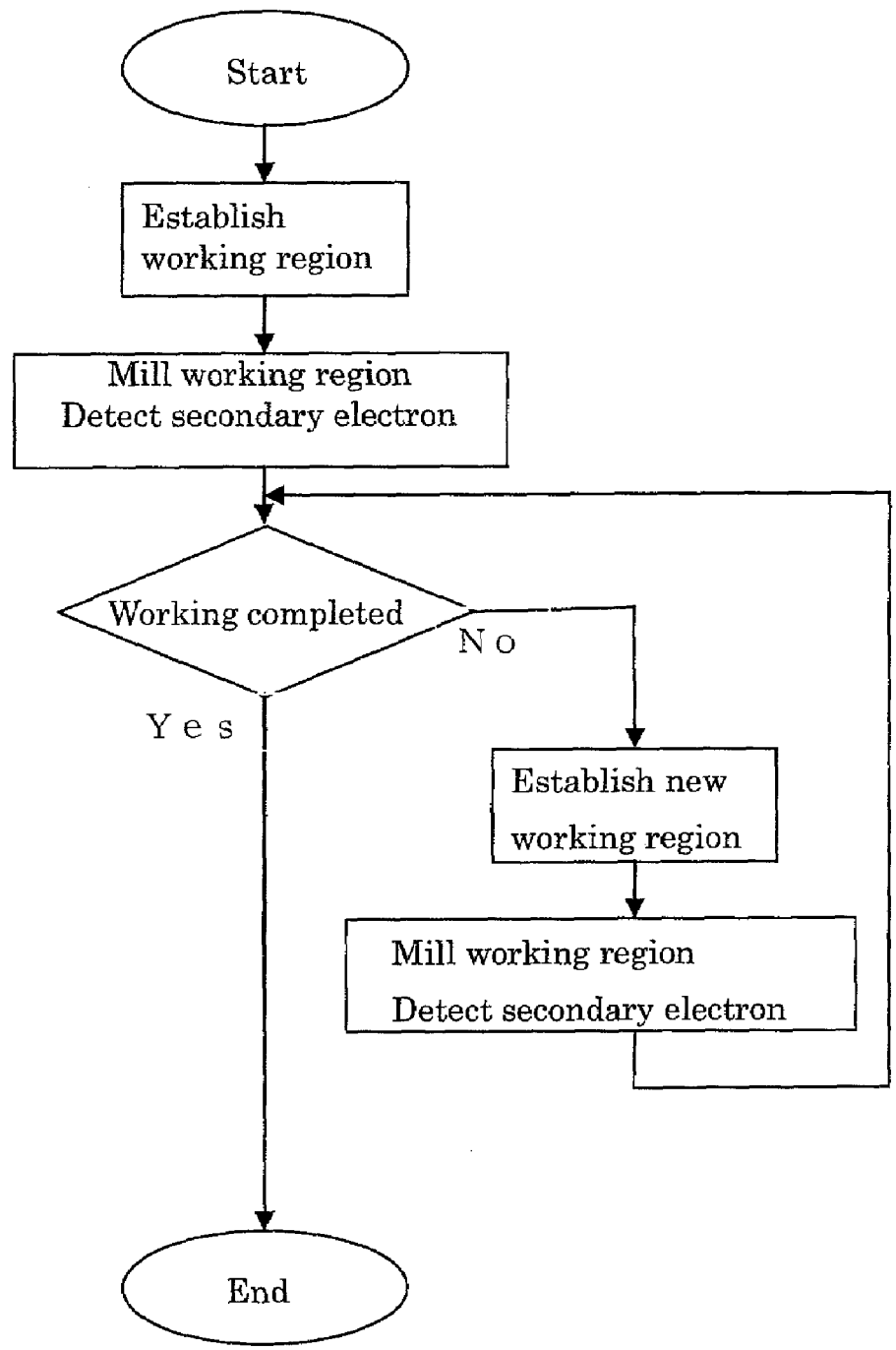
FIG. 6 is a flowchart showing the embodiment of the invention.
Figure 7:
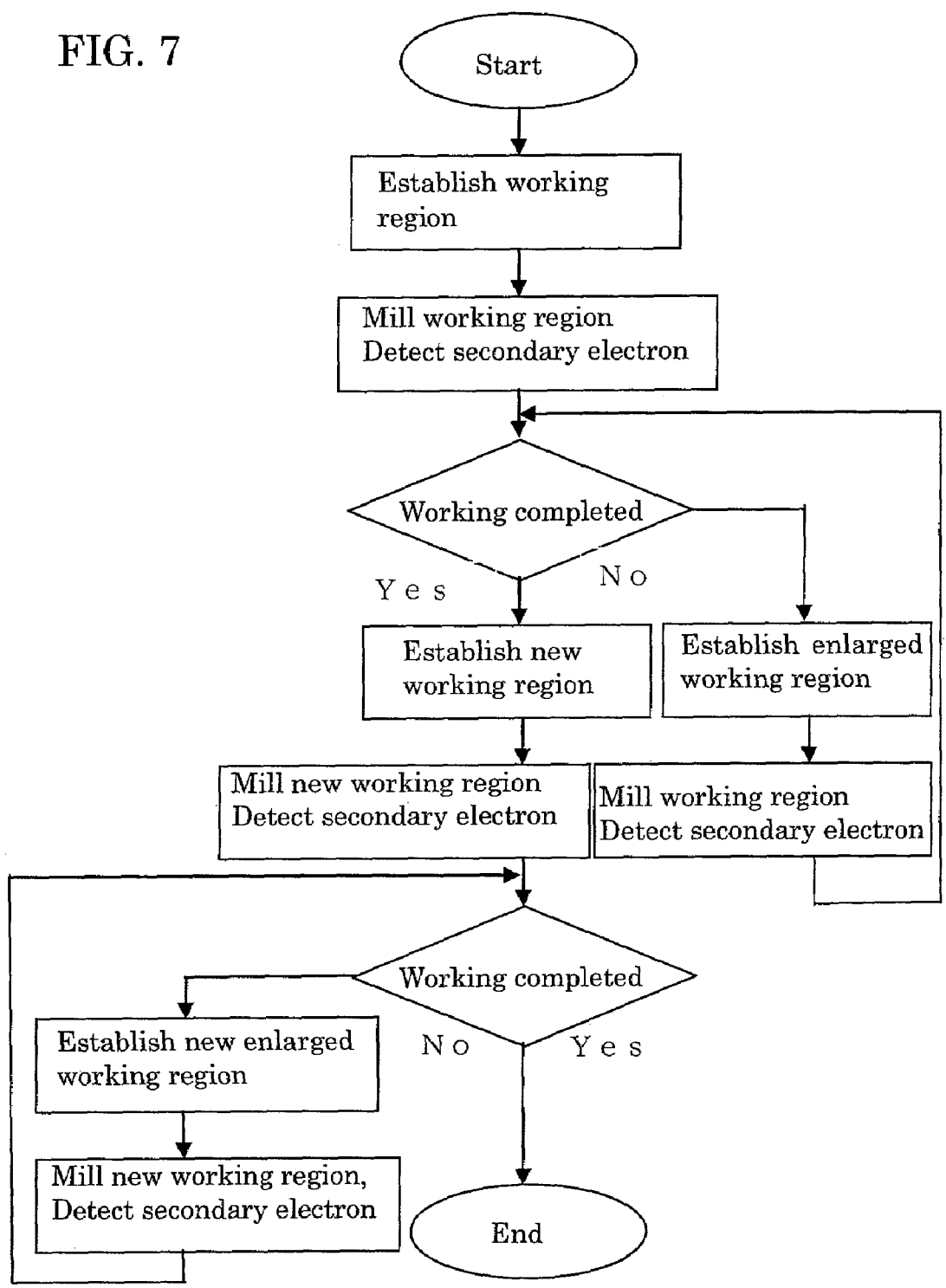
FIG. 7 is a flowchart showing the embodiment of the invention.

Using a flowchart in FIG. 6 illustrating the embodiment of the invention, explanation is made on a sample section forming method according to the invention. A secondary electron image is acquired as to the sample surface by moving the sample stage 13 to a position of the contact hole 7 by use of the coordinate information of a design layout figure and defect inspection apparatus. However, because the contact hole 7 is covered with a surface protection film 4, it is impossible to know a correct position of the contact hole 7 in the secondary electron image acquired. Using the acquired secondary electron image, a working region is established on the sample surface by estimating a position where the contact hole 7 can be worked in section.

Figure 2A:
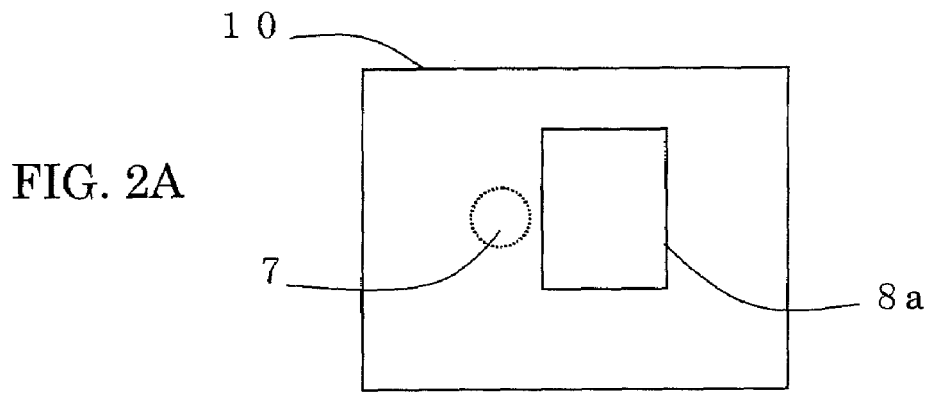
FIGS. 2A-2D are sample surface views showing the embodiment of the invention.

The working region 8a in FIG. 2A illustrates a case not in a position to work the contact hole 7 in section.

Then, the secondary electron 2, generated in etching, is detected while performing etching with scan-irradiation of a focused ion beam 1 to the established working region 8a wherein the direction nearly parallel with one side of the section is taken as a main scanning direction and the direction nearly vertical to the main scanning direction as a sub-scanning direction. As for the cumulative secondary-electron signal amount in this case, the cumulative secondary-electron signal amount is constant with respect to the main scanning direction in FIG. 3A.

Figure 2B:
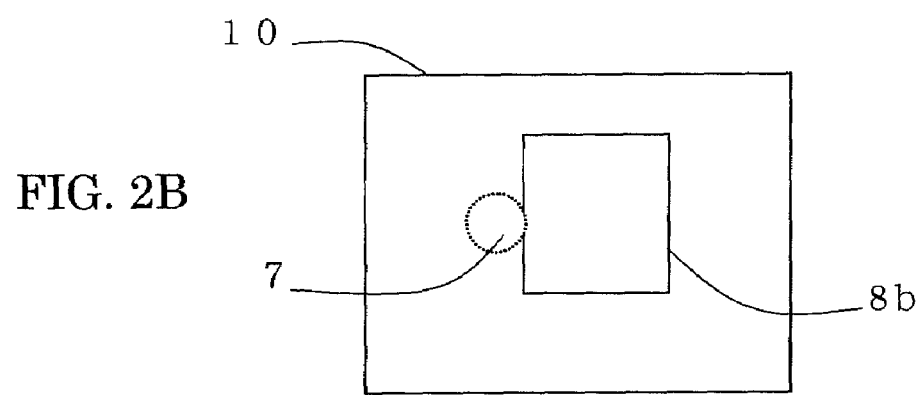

Then, in FIG. 2B, a working region 8b is established to newly work the contact hole 7 in its section, thereby performing etching on the working region. Concerning the secondary-electron signal amount detected and cumulated during the etching, the cumulative secondary electron amount changes in a certain position in FIG. 3B. The change of cumulative secondary-electron signal amount is attributable to illuminating a focused ion beam 1 to a part of the contact hole 7 in forming the working region 8B in FIG. 2B. Because the amount of the secondary electrons generated by irradiating a focused ion beam 1 differs from material to material, irradiating a focused ion beam 1 to the contact hole 7 changes the amount of secondary-electron signals in a position the contact hole 7 exists with respect to the main scanning direction of the focused ion beam 1, as in FIG. 3B.

Figure 2C:
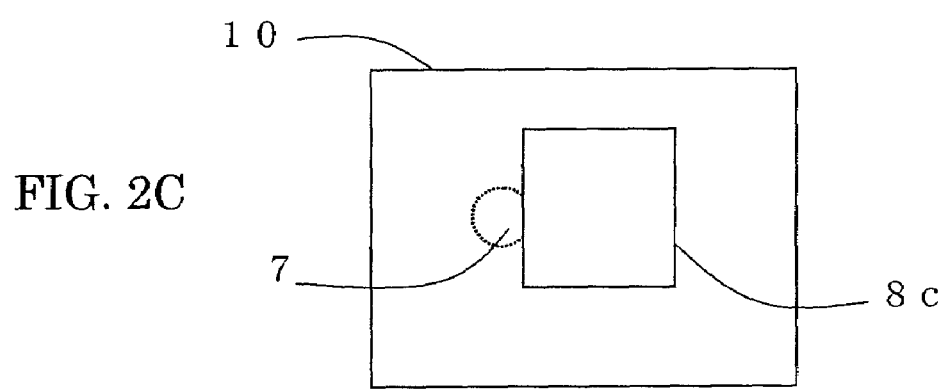

Furthermore, a new working region 8c is established as in FIG. 2C, to perform etching on the working region. The secondary-electron signal amount detected and cumulated during the etching is shown flat in FIG. 3C, at the tip of a secondary-electron signal amount peak. The flat portion represents an etching on the contact hole 7.

Figure 2D:
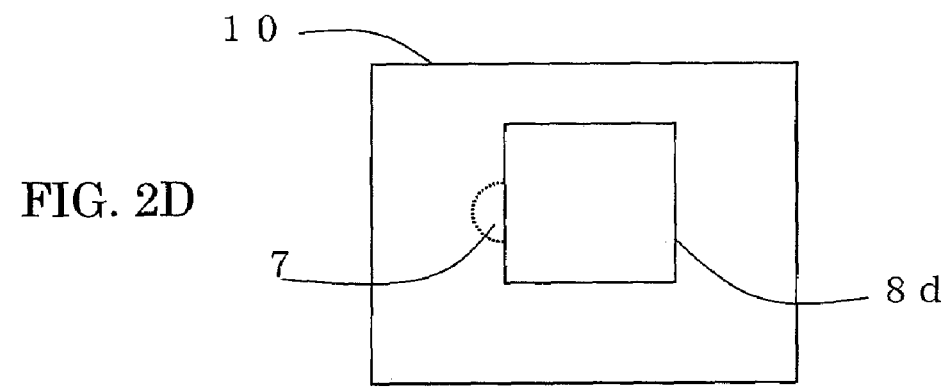
Figure 3A:
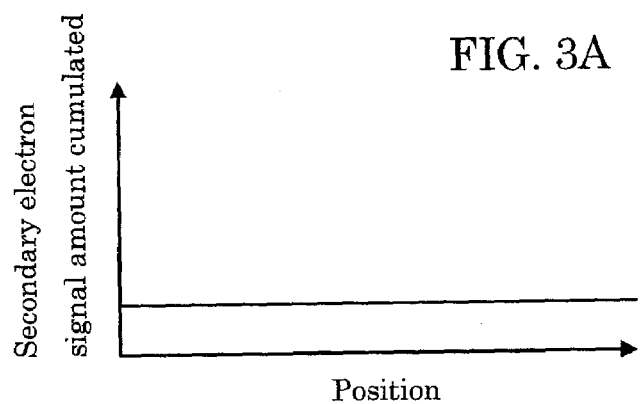
FIGS. 3A-3D show relationships between a position and a cumulative secondary-electron signal amount showing the embodiment of the invention.
Figure 3B:
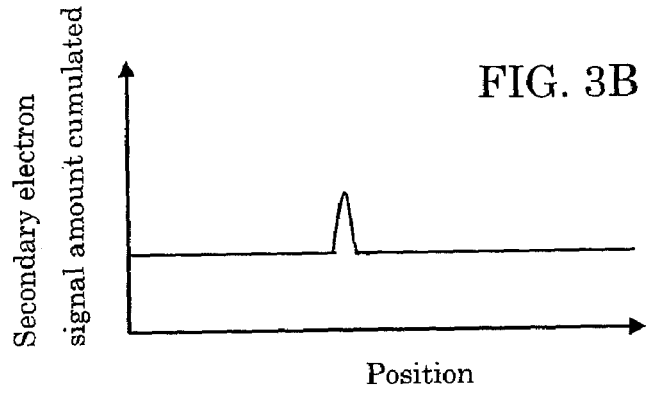
Figure 3C:
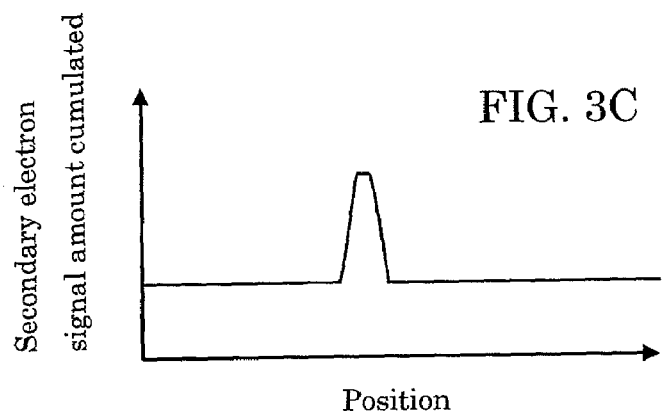
Figure 3D:
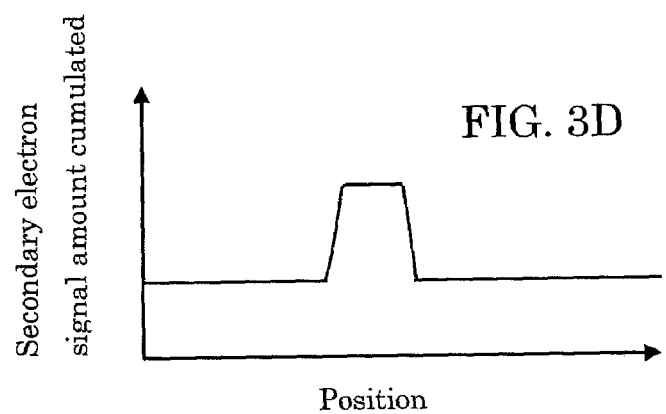

Furthermore, in FIG. 2D, a working region 8d is established to perform etching on the working region. The secondary-electron signal amount cumulated in this time is greater at its peak width than that of FIG. 3C, as in FIG. 3D. When this peak width becomes largest, the section of the contact hole made by the etching is considered lying in the diameter of the contact hole. It can be determined that etching has reached the center or the around of the contact hole. Here, the time the peak width is the greatest is to be determined as time the peak increase is the minimal in the course of observing the size of the peak due to forming. Then, the etching is finished. The above method allows for forming a section including the axis of the contact hole 7. Finally, the sample stage 13 is inclined to irradiate a focused ion beam 1 to the section thus formed. By scan-irradiating a focused ion beam 1 to the section, the section can be observed including the center axis of the contact hole 7.

Figure 4A:
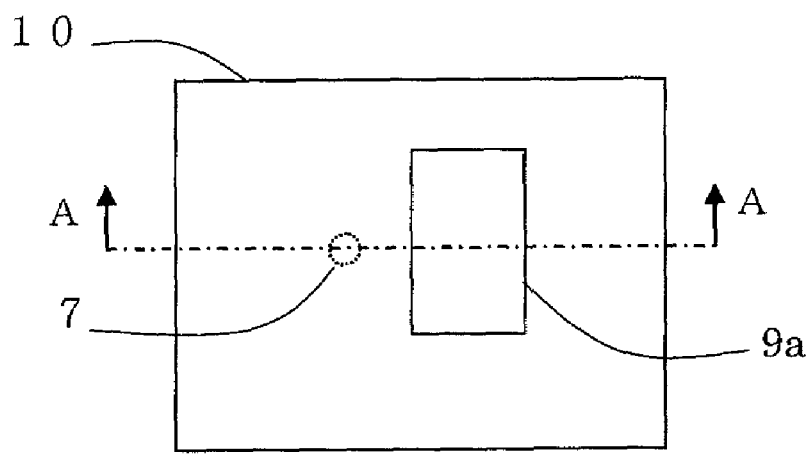
FIGS. 4A-4C are sample surface views showing the embodiment of the invention.
Figure 4B:
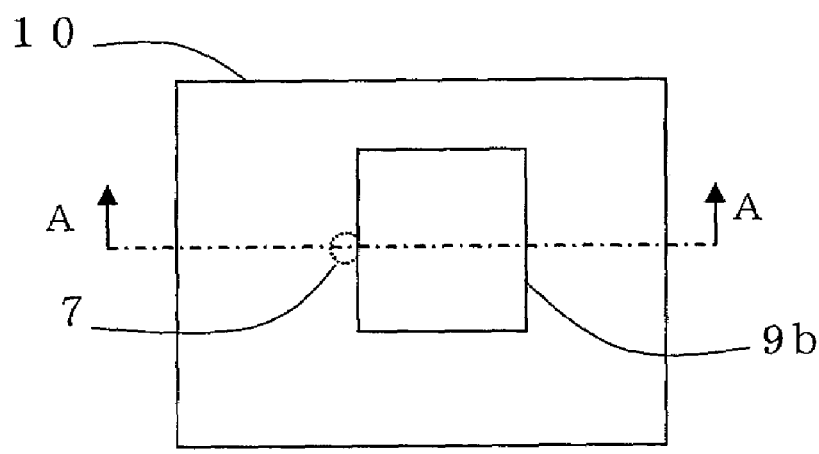
Figure 4C:
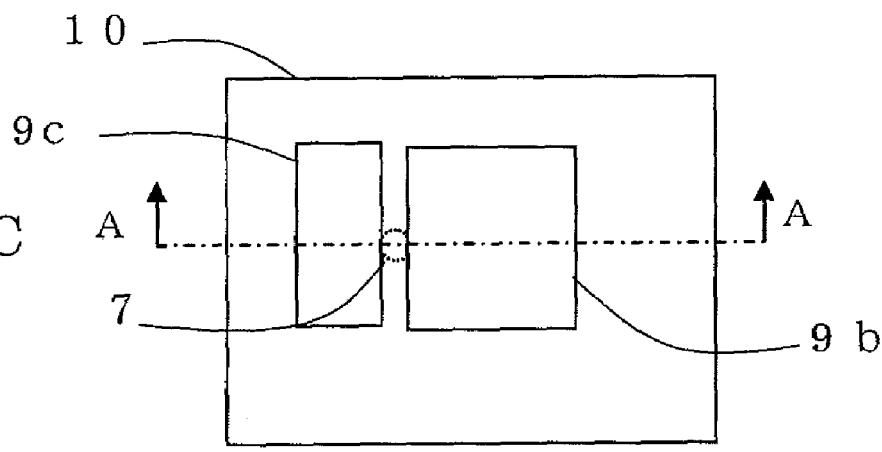
Figure 5A:
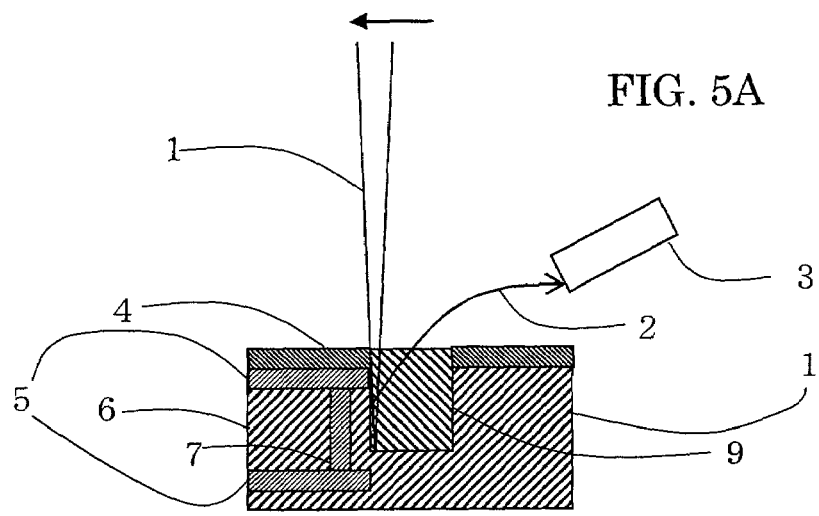
FIGS. 5A-5C are A-A sample sectional views of FIGS. 4A-4C.
Figure 5B:
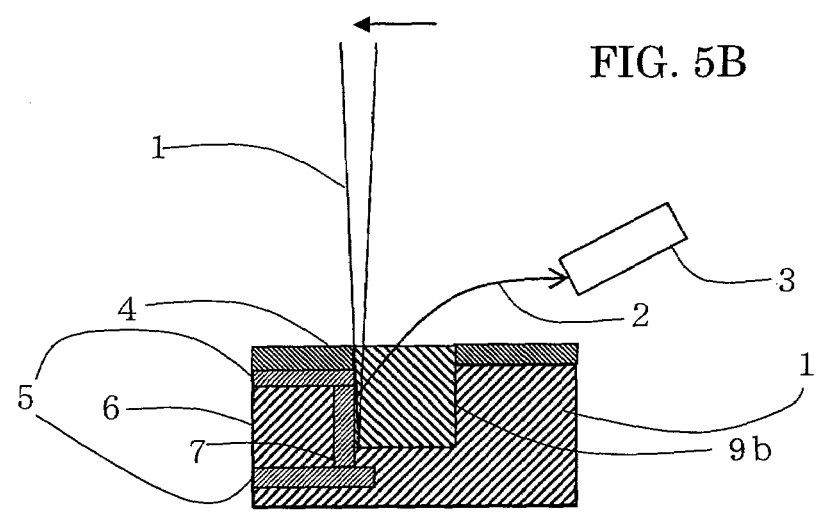
Figure 5C:
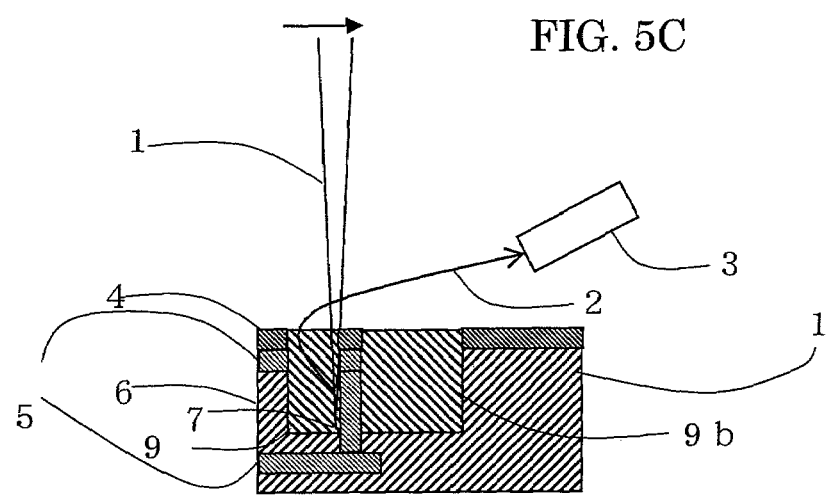

Using FIGS. 4A-4C, 5A-5C and 7, explanation is made on a case to prepare a thin-piece sample including the axis of a contact hole. FIGS. 4A-4C are sample surface views of a sample 10 including a contact hole. FIGS. 5A-5C are A-A sectional views of FIGS. 4A-4C. The sample 10 is structured with an interlayer film 6, interconnections 5 and a contact hole 7 connecting between the interconnections 5.

Explanation is made using a flowchart showing the embodiment of the invention. Using the coordinate information of a design layout figure and defect inspection apparatus, a working region is established on a sample surface. By irradiating a focused ion beam 1 to the established working region with scanning, etching is performed toward the contact hole 7 while forming a section starting from a position distant from the contact hole, thereby forming a trench 9a as in FIGS. 4A and 5A. In this case, etching is performed while confirming the secondary-electron signal amount just as in case of observing the section including the axis of a contact hole. When not observed a portion the secondary-electron signal changes in a position with respect to the section during forming a section by etching a trench 9a, a working region is established in a manner to broaden the working region as in FIGS. 4B and 5B, to form a trench 9b by etching. With the etching conducted while confirming the amount of secondary-electron signals, when a change point in the secondary electron signal amount is observed, etching is considered to have been conducted till reaching the contact hole 7 thus the forming of the trench 9 is terminated.

Then, a new working region is established in a position opposite to the trench 9b with respect to the contact hole 7, as shown in FIGS. 4C and 5C. Etching is made on the established working region similarly to the above method thereby forming a trench 9c. After confirming a change point in the signal amount of secondary electrons similarly to the forming of the trench 9b, etching is ended on the assumption that the trench 9c reached the contact hole 7. This can prepare a thin-piece sample including the center axis of the contact hole 7. Then, the thin-piece sample prepared is separated from the sample 10 in order to TEM-observe it and fixed on a TEM-observation sample holder, thus being transported to a TEM apparatus. By irradiating an electron beam vertically to the thin-piece sample on the TEM apparatus, a TEM image can be observed as to the thin-piece sample including the center axis of the contact hole 7.

Figure 8A:
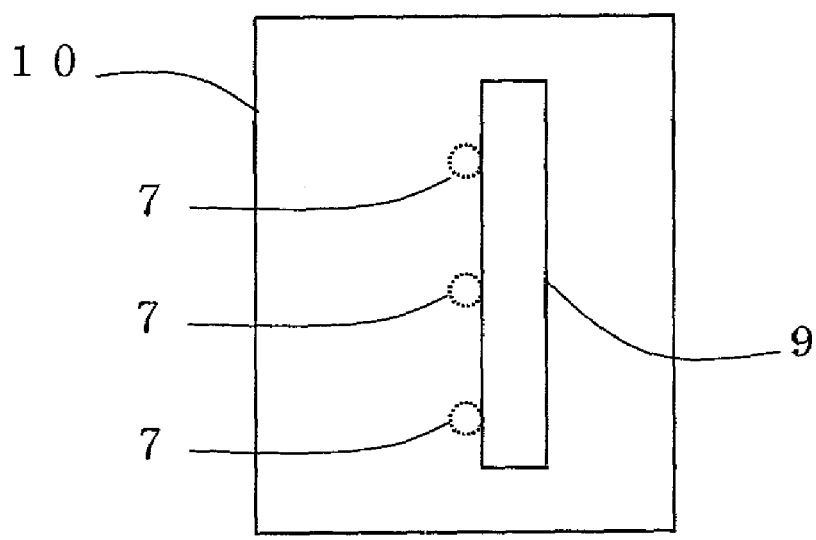
FIG. 8A is a sample surface view and FIG. 8B is a relationship between a position and a cumulative secondary-electron signal amount, showing the embodiment of the invention.
Figure 8B:
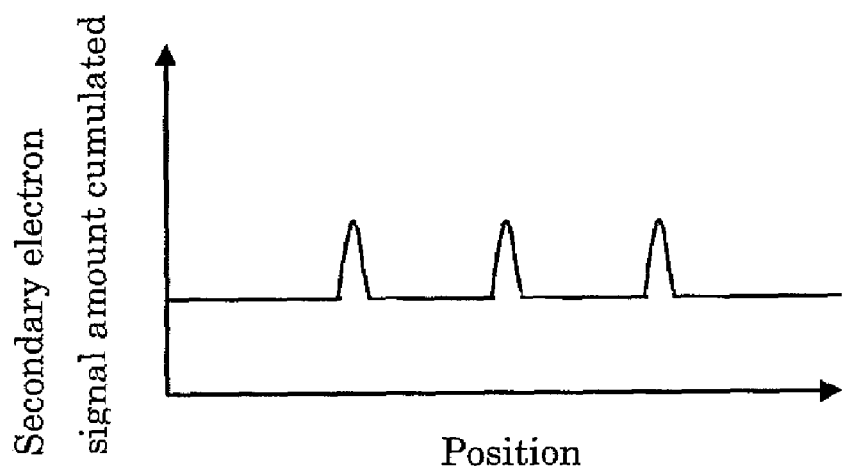
Figure 9:
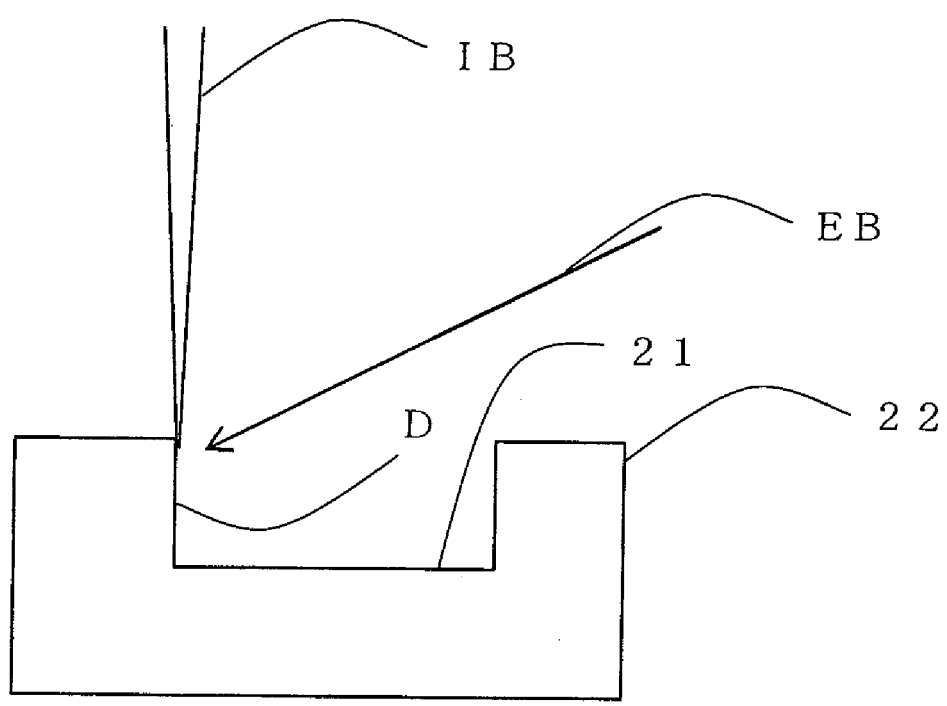
FIG. 9 is an FIB-SEM apparatus showing an embodiment in the prior art.

Meanwhile, explanation is made on a case to observe the section of a sample that contact holes are arranged at a constant interval. FIG. 8A is a sample surface view of a sample that contact holes 7 are arranged at a constant interval. In order to observe the section of the contact holes 7, a working region is established. A trench 9 is formed by scan-irradiating a focused ion beam 1 wherein main scanning direction is taken in a direction nearly parallel with one side of the section and sub-scanning direction in a direction nearly vertical to the main scanning direction. FIG. 8B shows a relationship between a position in this case and a cumulative signal amount of secondary electrons, wherein detected are peaks of cumulated secondary-electron signal amount matched to the interval of the contact holes 7. Due to this, where the interval of the contact holes 7 is known, the position of the contact hole 7 can be confirmed by examining the peak interval of the cumulated secondary-electron signal amount, thus enabling to determine an end point. Although sectional observation was explained herein, the use of the above method makes it possible to prepare a thin-piece sample including the center of a contact hole 7.

Although explanation was by use of a contact hole as an object to observe, the subject matter of the invention is not limited to the same. For example, the invention is to exhibit the effect also in sectionally observing a defect in a sample or preparing a TEM sample of a defective portion. Meanwhile, the secondary electron detecting example was explained as secondary charge particles, secondary ions can be used.

What is claimed is:

1. A method of forming a sample section containing at least two different materials with respect to a direction parallel with a sample surface by use of a focused ion beam apparatus, the sample section forming method using a focused ion beam apparatus comprising the steps of:

detecting secondary charged particles generated by irradiating the focused ion beam while performing etching on a desired region of a sample by scan-irradiating a focused ion beam to form a section vertically to the sample surface; and detecting changing amounts of signals based on the detected secondary charged particles and terminating the etching depending upon the changing amounts.

2. A sample section forming method using a focused ion beam apparatus according to claim 1, wherein the desired region is established to have one side nearly parallel with one side of the desired section in the sample surface, to perform etching in a manner forming a section including the parallel one side, followed by performing etching on the working region with scan-irradiating the focused ion beam while forming a section of the working region toward the desired section and in a direction broadening, so that a signal amount change at each sectional position is detected based on a signal of secondary charge particles generated at this time, depending upon a change amount of which the etching is terminated.

3. A sample section forming method using a focused ion beam apparatus according to claim 1, wherein the step of terminating the etching by detecting a signal amount change with the detected secondary charged particle signal includes cumulating with respect to the sub-scanning direction a secondary charged particle signal detected in the etching in a main scanning direction at each sub-scanning position provided that a direction nearly parallel with one side of the desired section is taken as the main scanning direction and a direction vertical to the main direction as the sub-scanning direction, detecting a change of the cumulated signal amount, and terminating the etching depending upon a change amount thereof.

4. A thin-piece sample preparing method using a focused ion beam apparatus comprising:

a step of forming a sample section by using a sample section forming method using a focused ion beam apparatus according to claim 1; and a step of forming similarly a section oppositely to the formed sample section with respect to a desired thin-piece sample region, to form a thin-piece sample region.

5. A focused ion beam apparatus comprising:

an ion generation source for generating ions;

an ion optical system that restricts the ions into a focused ion beam and irradiating, while scanning, the focused ion beam to the sample surface;

a sample table for supporting a sample;

a sample-table control mechanism for moving the sample table;

a secondary charged particle detector that detects a secondary charged particle generated by irradiating the focused ion beam; and an end-point detecting mechanism that detects an end point from the change amount of a secondary charged particle signal amount detected at the secondary charged particle detector when proceeding an etching on a section formed vertically to the sample surface by scan-irradiating the focused ion beam.

6. A method of forming a section in a sample surface by san-irradiating a focused ion beam in a direction parallel with an axis of a lens barrel of a focused ion beam apparatus and forming a sample section in a desired region of a sample while etching the section, the sample section forming method using a focused ion beam apparatus characterized by including:

a step of detecting a secondary charged particle generated by irradiating the focused ion beam; and a step of detecting a signal amount change of a detected signal of the secondary charged particle and terminating the etching depending upon the change amount when there is a change of signal amount.

\* \* \* \* \*